US005720962A

United States Patent [19]
Ivy et al.

[11] Patent Number: 5,720,962
[45] Date of Patent: Feb. 24, 1998

[54] ANALGESIC LOTION FOR HEMORRHOIDS AND METHOD OF MAKING SUCH LOTION

[75] Inventors: Jeffery Wade Ivy, Van Zandt County; Curtis Emery Payne, Smith County, both of Tex.; Christopher Dominic Burda, Caddo Parish, La.

[73] Assignee: Au Pharmaceuticals, Inc., Tyler, Tex.

[21] Appl. No.: 539,063

[22] Filed: Oct. 4, 1995

[51] Int. Cl.⁶ .................. A61K 9/00; A61K 7/48
[52] U.S. Cl. .............. 424/401; 424/195.1; 514/882
[58] Field of Search .................. 424/401, 195.1; 514/882

[56] References Cited

U.S. PATENT DOCUMENTS

| 4,192,866 | 3/1980 | Anderson | 424/154 |
| 4,797,392 | 1/1989 | Chernomorsky | 514/185 |
| 4,963,591 | 10/1990 | Fourman | 514/944 |
| 5,256,417 | 10/1993 | Koltisko | 424/402 |
| 5,376,374 | 12/1994 | Zelaya | 424/195.1 |
| 5,384,123 | 1/1995 | Metsada | 424/74 |
| 5,446,063 | 8/1995 | Reuter | 514/535 |

*Primary Examiner*—Sally Gardner-Lane
*Attorney, Agent, or Firm*—Frederick D. Hamilton

[57] ABSTRACT

This invention relates to an externally applied lotion that causes irritation or mild inflammation of the skin or mucous membranes for the purpose of relieving pain in hemorrhoids and the method of making such lotion. The formulation of the present invention contains ingredients to perform the five functions of vasoconstrictor, astringent, analgesic, antipruritic, and anesthetic. An alternate embodiment of the invention provides a formulation of the invention having a suitable viscosity to enable the lotion to be applied by a spray applicator directly to the site of application.

24 Claims, No Drawings

5,720,962

ANALGESIC LOTION FOR HEMORRHOIDS AND METHOD OF MAKING SUCH LOTION

BACKGROUND OF THE INVENTION

This invention relates to externally applied lotions that cause irritation or mild inflammation of the skin or mucous membranes for the purpose of relieving pain in hemorrhoids and other anorectal inflammation.

DISCLOSURE OF THE INVENTION

This invention provides an externally applied lotion for relieving pain in hemorrhoids and other anorectal inflammation and the method of making such lotion. The active ingredients of the invention perform the five functions of vasoconstrictor, astringent, analgesic, antipruritic, and anesthetic. An alternate embodiment of the invention provides a formulation of the invention having a suitable viscosity to enable the lotion to be applied by a spray applicator directly to the site of application.

OBJECTS OF THE INVENTION

It is an object of the present invention to provide an analgesic lotion containing a number of ingredients to relieve pain in hemorrhoids and a method of making such lotion.

It is an object of the invention to provide an analgesic lotion that gives temporary relief from the pain and burning sensations caused by inflamed hemorrhoidal tissues and other anorectal inflammation.

It is a further object of the invention to provide an analgesic lotion that gives temporary relief from local anorectal itching and discomfort associated with inflamed hemorrhoidal tissues and other anorectal inflammation.

It is an additional object of the invention to provide an analgesic lotion that can temporarily reduce the swelling associated with irritation in hemorrhoids and other anorectal disorders.

It is another object of the invention to provide an analgesic lotion that performs the five functions of a vasoconstrictor, astringent, analgesic, antipruritic, and anesthetic.

It is another object of the invention to provide an embodiment of the lotion of the invention that may be applied by a spray applicator directly to the site of application.

BEST MODE FOR CARRYING OUT THE INVENTION

In the preferred embodiment of the invention hamamelis water (witch hazel) is contained in the lotion in an amount from 9.0000 to 11.0000 parts by weight and, preferably, in an amount of about 10.0000 parts by weight.

Epinephrine hydrochloride is contained in the lotion in an amount from 0.0045 to 0.0055 parts by weight and, preferably, in an amount of about 0.0050 parts by weight.

Menthol crystals are contained in the lotion in an amount from 0.0900 to 0.1100 parts by weight and, preferably, in an amount of about 0.1000 parts by weight.

Aloe powder, such as that sold under the name Aloe Vera Phytogel 1:199, is contained in the lotion in an amount from 4.0653 to 4.9687 parts by weight and, preferably, in an amount of about 4.5170 parts by weight.

Purified water is contained in the lotion in an amount from 64.2907 to 78.5775 parts by weight and, preferably, in an amount of about 71.4341 parts by weight.

Carbomer, also known as carboxy polymethylene, such as that sold by B. F. Goodrich under the name Carbopol 1342, is contained in the lotion in an amount from 0.3499 to 0.4277 parts by weight and, preferably, in an amount of about 0.3888 parts by weight.

Propylene glycol, such as that sold by ARCO Chemical Company under the name Propylene Glycol USP, is contained in the lotion in an amount from 4.0000 to 4.8888 parts by weight and, preferably, in an amount of about 4.4444 parts by weight.

Methylparaben, also known as methyl hydroxybenzoate, such as that sold by NIPA Laboratories, Inc. under the name Nipa Esters methyl p-hydroxybenzoate, is contained in the lotion in an amount from 0.1000 to 0.1222 parts by weight and, preferably, in an amount of about 0.1111 parts by weight.

Propylparaben, also known as propyl hydroxybenzoate, is contained in the lotion in an amount from 0.1000 to 0.1222 parts by weight and, preferably, in an amount of about 0.1111 parts by weight.

Tetrasodium ethylenediaminetetraacetate (tetrasodium EDTA) is contained in the lotion in an amount from 0.1000 to 0.1222 parts by weight and, preferably, in an amount of about 0.1111 parts by weight.

Diethanolamine cetyl phosphate (DEA cetyl phosphate), such as that sold by Givaudan Corporation under the name Amphisol, is contained in the lotion in an amount from 0.7000 to 0.8555 parts by weight and, preferably, in an amount of about 0.7777 parts by weight.

Stearic acid is contained in the lotion in an amount from 1.0000 to 1.2222 parts by weight and, preferably, in an amount of about 1.1111 parts by weight.

Glyceryl stearate is contained in the lotion in an amount from 0.2500 to 0.3055 parts by weight and, preferably, in an amount of about 0.2777 parts by weight.

PEG 100 stearate is contained in the lotion in an amount from 0.2500 to 0.3055 parts by weight and, preferably, in an amount of about 0.2777 parts by weight.

C 12–15 alkyl benzoate, such as that sold by Finetex, Inc. under the name Finsolv TN, is contained in the lotion in an amount from 5.0000 to 6.1111 parts by weight and, preferably, in an amount of about 5.5555 parts by weight.

Jojoba oil, such as that sold by LIPO Chemicals, Inc. under the name Lipovol J., is contained in the lotion in an amount from 0.1000 to 0.1222 parts by weight and, preferably, in an amount of about 0.1111 parts by weight.

Ginseng American 1:1 PB (propylene glycol) is contained in the lotion in an amount from 0.2000 to 0.2444 parts by weight and, preferably, in an amount of about 0.2222 parts by weight.

Imidazolidinyl urea, such as that sold by Sutton Laboratories, Inc. under the name GERMALL 115, is contained in the lotion in an amount from 0.2000 to 0.2444 parts by weight and, preferably, in an amount of about 0.2222 parts by weight.

Triethanolamine is contained in the lotion in an amount from 0.2000 to 0.2444 parts by weight and, preferably, in an amount of about 0.2222 parts by weight.

This completes the description of the preferred embodiment of the invention. The active ingredient hamamelis water (witch hazel) performs the function of an astringent. The active ingredient epinephrine hydrochloride performs the function of a vasoconstrictor. The active ingredient menthol performs the three functions of an analgesic, antipruritic, and anesthetic. The preferred embodiment of the invention is in a lotion form which may be directly applied to the site of hemorrhoids or other anorectal inflammation.

The following example describes the steps to be followed in manufacturing the preferred embodiment of the invention.

Purified water in an amount from 64.2907 to 78.5775 parts by weight is supplied in a stainless steel kettle equipped with a mixer and a heat exchanger attached to the kettle for heating and cooling the ingredients in the kettle.

From 0.3499 to 0.4277 parts by weight carbomer is dusted onto the water and mixed into the water.

As soon as the carbomer and water are smooth and uniform, from 4.0653 to 4.9687 parts by weight aloe powder, from 4.0000 to 4.8888 parts by weight propylene glycol, from 0.1000 to 0.1222 parts by weight methylparaben, from 0.1000 to 0.1222 parts by weight propylparaben, and from 0.1000 to 0.1222 parts by weight tetrasodium ethylenediaminetetraacetate (tetrasodium EDTA) are added and mixed into the smooth and uniform mixture while heating to a temperature of 75° C.

Upon reaching a temperature of 75° C., from 0.7000 to 0.8555 parts by weight diethanolamine cetyl phosphate (DEA cetyl phosphate), from 1.0000 to 1.2222 parts by weight stearic acid, from 0.2500 to 0.3055 parts by weight glyceryl stearate, from 0.2500 to 0.3055 parts by weight PEG 100 stearate, and from 3.0000 to 3.6666 parts by weight C 12-15 alkyl benzoate is mixed into the 75° C. mixture.

The 75° C. mixture is then cooled to 55° C.

A solution having a temperature of 55° C. and obtained from 2.0000 to 2.4444 parts by weight C 12-15 alkyl benzoate, from 0.0900 to 0.1100 parts by weight menthol crystals is mixed into the 55° C. mixture.

The 55° C. mixture is then cooled to a temperature of no more than 45° C.

From 0.1000 to 0.1222 parts by weight jojoba oil, from 0.2000 to 0.2444 parts by weight ginseng American 1:1 propylene glycol, from 0.2000 to 0.2444 parts by weight imidazolidinyl urea, and from 0.2000 to 0.2444 parts by weight triethanolamine are then mixed into the 45° C. mixture.

From 9.0000 to 11.0000 parts by weight hamamelis water (witch hazel), from 0.0045 to 0.0055 parts epinephrine hydrochloride are then mixed into the 45° C. mixture.

This completes the description of the steps to be followed in manufacturing the preferred embodiment of the invention.

In a first alternative embodiment of the invention certain essential oils may be added to provide additional cooling and lubrication for the lotion. The first alternative embodiment of the invention comprises the formula of the preferred embodiment of the invention together with the following essential oils.

The essential oil Vanilla (from the botanical species *Vanilla planifolia*) is contained in the first alternative embodiment of the lotion in an amount of from 0.5400 to 0.6600 parts by weight and, preferably, in an amount of about 0.6000 by weight.

The essential oil Hyssop (from the botanical species *Hyssopus officinalis*) is contained in the first alternative embodiment of the lotion in an amount of from 0.0900 to 0.1100 parts by weight and, preferably, in an amount of about 0.1000 by weight.

The essential oil Melissa (from the botanical species *Melissa officinalis*) is contained in the first alternative embodiment of the lotion in an amount of from 0.0900 to 0.1100 parts by weight and, preferably, in an amount of about 0.1000 by weight.

The essential oil Angelica (from the botanical species *Angelica archangelia*) is contained in the first alternative embodiment of the lotion in an amount of from 0.0900 to 0.1100 parts by weight and, preferably, in an amount of about 0.1000 by weight.

The essential oil Lavender (from the botanical species *Lavendula officinalis*) is contained in the first alternative embodiment of the lotion in an amount of from 0.0900 to 0.1100 parts by weight and, preferably, in an amount of about 0.1000 by weight.

In this first alternative embodiment of the invention the amount of purified water is adjusted to be from 63.3906 to 77.4774 parts by weight instead of from 64.2907 to 78.5775 parts by weight in order to accommodate the added volume of the essential oils. During the manufacturing process, the essential oils are added to the lotion after the epinephrine hydrochloride is added.

This completes the description of the first alternative embodiment of the invention.

In further alternative embodiments of the invention the ingredient gingko may be added to the formulation. In these alternative embodiments of the invention gingko is contained in the lotion in an amount from 0.2000 to 0.2444 parts by weight and, preferably, in an amount of about 0.2222 parts by weight. The amount of purified water in each alternative embodiment is adjusted to compensate for the weight of the gingko. During the manufacturing process, the gingko is added to the lotion when the ginseng is added.

Adding 0.2000 to 0.2444 parts by weight of gingko to the first alternative embodiment of the invention will cause the amount of purified water in this second alternative embodiment of the invention to be present in an amount from 63.1908 to 77.2330 parts by weight and, preferably, in an amount of about 70.2119 parts by weight.

Adding 0.2000 to 0.2444 parts by weight of gingko to the preferred embodiment of the invention will cause the amount of purified water in this third alternative embodiment of the invention to be present in an amount from 64.0908 to 78.3330 parts by weight and, preferably, in an amount of about 71.2119 parts by weight.

In a fourth alternative embodiment of the invention the active ingredient epinephrine hydrochloride may be replaced by the active ingredient ephedrine sulfate. In this fourth alternative embodiment of the invention ephedrine sulfate is contained in the lotion in an amount from 0.2250 to 0.2750 parts by weight and, preferably, in an amount of about 0.2500 parts by weight. The amount of hamamelis water is contained in the lotion in an amount from 22.5000 to 27.5000 parts by weight and, preferably, in an amount of about 25.0000 parts by weight. The amount of purified water in this fourth alternative embodiment of the invention is then adjusted to be present in an amount from 50.5701 to 61.8079 parts by weight and, preferably, in an amount of about 56.1890 parts by weight. The other ingredients are present in the same amounts are they are in the preferred embodiment of the invention.

The following example describes the steps to be followed in manufacturing this fourth alternative embodiment of the invention.

Purified water in an amount from 63.3906 to 77.4774 parts by weight is supplied in a stainless steel kettle equipped with a mixer and a heat exchanger attached to the kettle for heating and cooling the ingredients in the kettle.

From 0.3499 to 0.4277 parts by weight carbomer is dusted onto the water and mixed into the water.

As soon as the carbomer and water are smooth and uniform, from 4.0653 to 4.9687 parts by weight aloe powder, from 4.0000 to 4.8888 parts by weight propylene glycol, from 0.1000 to 0.1222 parts by weight methylparaben, from 0.1000 to 0.1222 parts by weight propylparaben, and from 0.1000 to 0.1222 parts by weight tetrasodium ethylenediaminetetraacetate (tetrasodium EDTA) are added and mixed into the smooth and uniform mixture while heating to a temperature of 75° C.

Upon reaching a temperature of 75° C., from 0.7000 to 0.8555 parts by weight diethanolamine cetyl phosphate (DEA cetyl phosphate), from 1.0000 to 1.2222 parts by weight stearic acid, from 0.2500 to 0.3055 parts by weight glyceryl stearate, from 0.2500 to 0.3055 parts by weight PEG 100 stearate, and from 3.0000 to 3.6666 parts by weight C 12–15 alkyl benzoate are mixed into the 75° C. mixture.

The 75° C. mixture is then cooled to 55° C.

A solution having a temperature of 55° C. and obtained from 2.0000 to 2.4444 parts by weight C 12–15 alkyl benzoate, from 0.0900 to 0.1100 parts by weight menthol crystals is mixed into the 55° C. mixture.

The 55° C. mixture is then cooled to a temperature of no more than 45° C.

From 0.1000 to 0.1222 parts by weight jojoba oil, from 0.2000 to 0.2444 parts by weight ginseng American 1:1 propylene glycol, from 0.2000 to 0.2444 parts by weight imidazolidinyl urea, from 0.2000 to 0.2444 parts by weight triethanolamine are then mixed into the 45° C. mixture.

From 9.0000 to 11.0000 parts by weight hamamelis water (witch hazel), from 0.0045 to 0.0055 parts epinephrine hydrochloride are then mixed into the 45° C. mixture.

From 0.5400 to 0.6600 parts by weight vanilla, from 0.0900 to 0.1100 parts hyssop, from 0.0900 to 0.1100 parts melissa, from 0.0900 to 0.1100 parts angelica, from 0.0900 to 0.1100 parts lavender, are then mixed into the 45° C. mixture.

This completes the description of the steps to be followed in manufacturing the fourth alternative embodiment of the invention.

A fifth alternative embodiment of the invention may be formed by adding gingko to the formulation of the fourth alternative embodiment of the invention. Adding 0.2000 to 0.2444 parts by weight of gingko, and preferably, in an amount of about 0.2222 parts by weight, to the fourth alternative embodiment of the invention will require the amount of purified water in this fifth alternative embodiment of the invention to be adjusted to be present in an amount from 63.1908 to 77.2330 parts by weight and, preferably, in an amount of about 70.2119 parts by weight. During the manufacturing process, the gingko is added to the lotion when the ginseng is added.

A sixth alternative embodiment of the invention provides a formulation of the invention having a suitable viscosity to enable the lotion to be applied by a spray applicator directly to the site of application.

In the sixth alternative embodiment of the invention hamamelis water (witch hazel) is contained in the lotion in an amount from 9.0000 to 11.0000 parts by weight and, preferably, in an amount of about 10.0000 parts by weight.

Epinephrine hydrochloride is contained in the lotion in an amount from 0.0045 to 0.0055 parts by weight and, preferably, in an amount of about 0.0050 parts by weight.

Menthol crystals are contained in the lotion in an amount from 0.0900 to 0.1100 parts by weight and, preferably, in an amount of about 0.1000 parts by weight.

Aloe powder, such as that sold under the name Aloe Vera Phytogel 1:199, is contained in the lotion in an amount from 4.0500 to 4.9500 parts by weight and, preferably, in an amount of about 4.5000 parts by weight.

Purified water is contained in the lotion in an amount from 61.2405 to 74.8495 parts by weight and, preferably, in an amount of about 68.0450 parts by weight.

Carbomer, also known as carboxy polymethylene, such as that sold by B. F. Goodrich under the name Carbopol 1342, is contained in the lotion in an amount from 4.5000 to 5.5000 parts by weight and, preferably, in an amount of about 5.0000 parts by weight.

Propylene glycol, such as that sold by ARCO Chemical Company under the name Propylene Glycol USP, is contained in the lotion in an amount from 3.6000 to 4.4000 parts by weight and, preferably, in an amount of about 4.0000 parts by weight.

Methylparaben, also known as methyl hydroxybenzoate, such as that sold by NIPA Laboratories, Inc. under the name Nipa Esters methyl p-hydroxybenzoate, is contained in the lotion in an amount from 0.1800 to 0.2200 parts by weight and, preferably, in an amount of about 0.2000 parts by weight.

Propylparaben, also known as propyl hydroxybenzoate, is contained in the lotion in an amount from 0.0900 to 0.1100 parts by weight and, preferably, in an amount of about 0.1000 parts by weight.

Tetrasodium ethylenediaminetetraacetate (tetrasodium EDTA) is contained in the lotion in an amount from 0.0900 to 0.1100 parts by weight and, preferably, in an amount of about 0.1000 parts by weight.

Diethanolamine cetyl phosphate (DEA cetyl phosphate), such as that sold by Givaudan Corporation under the name Amphisol, is contained in the lotion in an amount from 0.9000 to 1.1000 parts by weight and, preferably, in an amount of about 1.0000 parts by weight.

Stearic acid is contained in the lotion in an amount from 0.9000 to 1.1000 parts by weight and, preferably, in an amount of about 1.0000 parts by weight.

C 12–15 alkyl benzoate, such as that sold by Finetex, Inc. under the name Finsolv TN, is contained in the lotion in an amount from 4.5000 to 5.5000 parts by weight and, preferably, in an amount of about 5.0000 parts by weight.

Jojoba oil, such as that sold by LIPO Chemicals, Inc. under the name Lipovol J., is contained in the lotion in an amount from 0.0900 to 0.1100 parts by weight and, preferably, in an amount of about 0.1000 parts by weight.

Ginseng American 1:1 PB (propylene glycol) is contained in the lotion in an amount from 0.1800 to 0.2200 parts by weight and, preferably, in an amount of about 0.2000 parts by weight.

Imidazolidinyl urea, such as that sold by Sutton Laboratories, Inc. under the name GERMALL 115, is contained in the lotion in an amount from 0.1350 to 0.1650 parts by weight and, preferably, in an amount of about 0.1500 parts by weight.

Triethanolamine is contained in the lotion in an amount from 0.4500 to 0.5500 parts by weight and, preferably, in an amount of about 0.5000 parts by weight.

This completes the description of the sixth alternative embodiment of the invention. The active ingredient hammamelis water (witch hazel) performs the function of an astringent. The active ingredient epinephrine hydrochloride performs the function of a vasoconstrictor. The active ingredient menthol performs the three functions of an analgesic, antipruritic, and anesthetic.

The following example describes the steps to be followed in manufacturing the sixth alternative embodiment of the invention.

Purified water in an amount from 61.2405 to 74.8495 parts by weight is supplied in a stainless steel kettle equipped with a mixer and a heat exchanger attached to the kettle for heating and cooling the ingredients in the kettle.

From 4.5000 to 5.5000 parts by weight carbomer is dusted onto the water and mixed into the water.

As soon as the carbomer and water are smooth and uniform, from 9.0000 to 11.0000 parts by weight hamamelis water (witch hazel), from 4.0500 to 4.9500 parts by weight aloe powder, from 3.6000 to 4.4000 parts by weight propylene glycol, from 0.1800 to 0.2200 parts by weight methylparaben, from 0.0900 to 0.1100 parts by weight tetrasodium ethylenediaminetetraacetate (tetrasodium EDTA) are added and mixed into the smooth and uniform mixture while heating to a temperature of 75° C. This solution is referred to as the "phase A" mixture.

A second mixture referred to as the "phase B" mixture is mixed as follows. From 0.9000 to 1.1000 parts by weight diethanolamine cetyl phosphate (DEA cetyl phosphate) is mixed with from 0.9000 to 1.1000 parts by weight stearic acid. Then from 4.5000 to 5.5000 parts by weight C 12–15 alkyl benzoate, and from 0.0900 to 0.1100 parts by weight jojoba oil, and from 0.1800 to 0.2200 parts by weight ginseng, and from 0.0900 to 0.1100 parts by weight propylparaben are added and mixed into the "phase B" mixture while heating to a temperature of 75° C.

The "phase B" mixture is then mixed into the "phase A" mixture creating a "phase C" mixture. From 0.4500 to 0.5500 parts by weight of triethanolamine is then mixed into the "phase C" mixture. The "phase C" mixture is then mixed for about ten minutes at a temperature of approximately 75° C. The "phase C" mixture is then cooled to 40° C.

From 0.0900 to 0.1100 parts by weight of menthol crystals is then mixed into the "phase C" mixture.

A "phase D" mixture is then created by mixing from 0.0045 to 0.0055 parts by weight epinephrine hydrochloride and from 0.1350 to 0.1650 parts by weight imidazolidinyl urea at a temperature of approximately 40° C. The "phase D" mixture is then mixed into the "phase C" mixture to create the final mixture. The final mixture is then cooled to approximately 25° C.

This completes the description of the steps to be followed in manufacturing the sixth alternative embodiment of the invention.

In a seventh alternative embodiment of the invention certain essential oils may be added to provide additional cooling and lubrication for the lotion. The seventh alternative embodiment of the invention comprises the formula of the sixth alternative embodiment of the invention together with the following essential oils.

The essential oil Vanilla (from the botanical species *Vanilla planifolia*) is contained in the seventh alternative embodiment of the lotion in an amount of from 0.0900 to 0.1100 parts by weight and, preferably, in an amount of about 0.1000 by weight.

The essential oil Hyssop (from the botanical species *Hyssopus officinalis*) is contained in the seventh alternative embodiment of the lotion in an amount of from 0.0450 to 0.0550 parts by weight and, preferably, in an amount of about 0.0500 by weight.

The essential oil Melissa (from the botanical species *Melissa officinalis*) is contained in the seventh alternative embodiment of the lotion in an amount of from 0.0450 to 0.0550 parts by weight and, preferably, in an amount of about 0.0500 by weight.

The essential oil Angelica (from the botanical species *Angelica archangelia*) is contained in the seventh alternative embodiment of the lotion in an amount of from 0.0450 to 0.0550 parts by weight and, preferably, in an amount of about 0.0500 by weight.

The essential oil Lavender (from the botanical species *Lavendula officinalis*) is contained in the seventh alternative embodiment of the lotion in an amount of from 0.0450 to 0.0550 parts by weight and, preferably, in an amount of about 0.0500 by weight.

In this seventh alternative embodiment of the invention the amount of purified water is adjusted to be from 60.9705 to 74.5195 parts by weight instead of from 61.2405 to 74.8495 parts by weight in order to accommodate the added volume of the essential oils.

The following example describes the steps to be followed in manufacturing the seventh alternative embodiment of the invention.

Purified water in an amount from 60.9705 to 74.5195 parts by weight is supplied in a stainless steel kettle equipped with a mixer and a heat exchanger attached to the kettle for heating and cooling the ingredients in the kettle.

From 4.5000 to 5.5000 parts by weight carbomer is dusted onto the water and mixed into the water.

As soon as the carbomer and water are smooth and uniform, from 9.0000 to 11.0000 parts by weight hamamelis water (witch hazel), from 4.0500 to 4.9500 parts by weight aloe powder, from 3.6000 to 4.4000 parts by weight propylene glycol, from 0.1800 to 0.2200 parts by weight methylparaben, from 0.0900 to 0.1100 parts by weight tetrasodium ethylenediaminetetraacetate (tetrasodium EDTA) are added and mixed into the smooth and uniform mixture while heating to a temperature of 75° C. This solution is referred to as the "phase A" mixture.

A second mixture referred to as the "phase B" mixture is mixed as follows. From 0.9000 to 1.1000 parts by weight diethanolamine cetyl phosphate (DEA cetyl phosphate) is mixed with from 0.9000 to 1.1000 parts by weight stearic acid. Then from 4.5000 to 5.5000 parts by weight C 12–15 alkyl benzoate, and from 0.0900 to 0.1100 parts by weight jojoba oil, and from 0.1800 to 0.2200 parts by weight ginseng, and from 0.0450 to 0.0550 parts by weight hyssop, and from 0.0450 to 0.0550 parts by weight melissa, and from 0.0450 to 0.0550 parts by weight angelica, and from 0.0900 to 0.1100 parts by weight propylparaben are added and mixed into the "phase B" mixture while heating to a temperature of 75° C.

The "phase B" mixture is then mixed into the "phase A" mixture creating a "phase C" mixture. From 0.4500 to 0.5500 parts by weight of triethanolamine is then mixed into the "phase C" mixture. The "phase C" mixture is then mixed for about ten minutes at a temperature of approximately 75° C. The "phase C" mixture is then cooled to 40° C.

A "phase D" mixture is then created by mixing from 0.0900 to 0.1100 parts by weight of menthol crystals and from 0.0900 to 0.1100 parts by weight vanilla and from 0.0450 to 0.0550 parts by weight lavender at a temperature of approximately 40° C. The "phase D" mixture of menthol and vanilla and lavender is then mixed into the "phase C" mixture to create a new "phase D" mixture consisting of the "phase C" mixture and menthol and vanilla and lavender.

A "phase E" mixture is then created by mixing from 0.0045 to 0.0055 parts by weight epinephrine hydrochloride and from 0.1350 to 0.1650 parts by weight imidazolidinyl urea at a temperature of approximately 40° C. The "phase E" mixture is then mixed into the "phase D" mixture to create the final mixture. The final mixture is then cooled to approximately 25° C.

This completes the description of the steps to be followed in manufacturing the seventh alternative embodiment of the invention.

Although the description above contains very specific formulae for embodiments of the invention, these should not be construed as limiting the scope of the invention but as merely providing illustrations of some of the presently preferred embodiments of this invention. Thus the scope of the invention should be determined by the appended claims and their legal equivalents, rather than by the examples given.

The invention having been described, what is claimed is:

1. A lotion comprising: from 9.0000 to 11.0000 parts by weight hamamelis water; from 0.0045 to 0.0055 parts by weight epinephrine hydrochloride; from 0.0900 to 0.1100 parts by weight menthol crystals; from 4.0653 to 4.9687 parts by weight aloe powder; from 64.2907 to 78.5775 parts by weight purified water; from 0.3499 to 0.4277 parts by weight carbomer; from 4.0000 to 4.8888 parts by weight propylene glycol; from 0.1000 to 0.1222 parts by weight methylparaben; from 0.1000 to 0.1222 parts by weight propylparaben; from 0.1000 to 0.1222 parts by weight tetrasodium EDTA; from 0.7000 to 0.8555 parts by weight DEA cetyl phosphate; from 1.0000 to 1.2222 parts by weight stearic acid; from 0.2500 to 0.3055 parts by weight glyceryl stearate; from 0.2500 to 0.3055 parts by weight PEG 100 stearate; from 5.0000 to 6.1111 parts by weight C 12–15 alkyl benzoate; from 0.1000 to 0.1222 parts by weight jojoba oil; from 0.2000 to 0.2444 parts by weight ginseng; from 0.2000 to 0.2444 parts by weight imidazolidinyl urea; and from 0.2000 to 0.2444 parts by weight triethanolamine.

2. A lotion comprising: from 9.0000 to 11.0000 parts by weight hamamelis water; from 0.0045 to 0.0055 parts by weight epinephrine hydrochloride; from 0.0900 to 0.1100 parts by weight menthol crystals; from 4.0653 to 4.9687 parts by weight aloe powder; from 63.3906 to 77.4774 parts by weight purified water; from 0.3499 to 0.4277 parts by weight carbomer; from 4.0000 to 4.8888 parts by weight propylene glycol; from 0.1000 to 0.1222 parts by weight methylparaben; from 0.1000 to 0.1222 parts by weight propylparaben; from 0.1000 to 0.1222 parts by weight tetrasodium EDTA; from 0.7000 to 0.8555 parts by weight DEA cetyl phosphate; from 1.0000 to 1.2222 parts by weight stearic acid; from 0.2500 to 0.3055 parts by weight glyceryl stearate; from 0.2500 to 0.3055 parts by weight PEG 100 stearate; from 5.0000 to 6.1111 parts by weight C 12–15 alkyl benzoate; from 0.1000 to 0.1222 parts by weight jojoba oil; from 0.2000 to 0.2444 parts by weight ginseng; from 0.2000 to 0.2444 parts by weight imidazolidinyl urea; and from 0.2000 to 0.2444 parts by weight triethanolamine; from 0.5400 to 0.6600 parts by weight vanilla; and from 0.0900 to 0.1100 parts by weight hyssop; from 0.0900 to 0.1100 parts by weight melissa; and from 0.0900 to 0.1100 parts by weight angelica; and from 0.0900 to 0.1100 parts by weight lavender.

3. A lotion comprising: from 9.0000 to 11.0000 parts by weight hamamelis water; from 0.0045 to 0.0055 parts by weight epinephrine hydrochloride; from 0.0900 to 0.1100 parts by weight menthol crystals; from 4.0653 to 4.9687 parts by weight aloe powder; from 63.1908 to 77.2330 parts by weight purified water; from 0.3499 to 0.4277 parts by weight carbomer; from 4.0000 to 4.8888 parts by weight propylene glycol; from 0.1000 to 0.1222 parts by weight methylparaben; from 0.1000 to 0.1222 parts by weight propylparaben; from 0.1000 to 0.1222 parts by weight tetrasodium EDTA; from 0.7000 to 0.8555 parts by weight DEA cetyl phosphate; from 1.0000 to 1.2222 parts by weight stearic acid; from 0.2500 to 0.3055 parts by weight glyceryl stearate; from 0.2500 to 0.3055 parts by weight PEG 100 stearate; from 5.0000 to 6.1111 parts by weight C 12–15 alkyl benzoate; from 0.1000 to 0.1222 parts by weight jojoba oil; from 0.2000 to 0.2444 parts by weight ginseng; from 0.2000 to 0.2444 parts by weight imidazolidinyl urea; and from 0.2000 to 0.2444 parts by weight triethanolamine; from 0.5400 to 0.6600 parts by weight vanilla; and from 0.0900 to 0.1100 parts by weight hyssop; from 0.0900 to 0.1100 parts by weight melissa; and from 0.0900 to 0.1100 parts by weight angelica; from 0.0900 to 0.1100 parts by weight lavender; and from 0.2000 to 0.2444 parts by weight gingko.

4. A lotion comprising: from 9.0000 to 11.0000 parts by weight hamamelis water; from 0.0045 to 0.0055 parts by weight epinephrine hydrochioride; from 0.0900 to 0.1100 parts by weight menthol crystals; from 4.0653 to 4.9687 parts by weight aloe powder; from 64.0908 to 78.3330 parts by weight purified water; from 0.3499 to 0.4277 parts by weight carbomer; from 4.0000 to 4.8888 parts by weight propylene glycol; from 0.1000 to 0.1222 parts by weight methylparaben; from 0.1000 to 0.1222 parts by weight propylparaben; from 0.1000 to 0.1222 parts by weight tetrasodium EDTA; from 0.7000 to 0.8555 parts by weight DEA cetyl phosphate; from 1.0000 to 1.2222 parts by weight stearic acid; from 0.2500 to 0.3055 parts by weight glyceryl stearate; from 0.2500 to 0.3055 parts by weight PEG 100 stearate; from 5.0000 to 6.1111 parts by weight C 12–15 alkyl benzoate; from 0.1000 to 0.1222 parts by weight jojoba oil; from 0.2000 to 0.2444 parts by weight ginseng; from 0.2000 to 0.2444 parts by weight imidazolidinyl urea; and from 0.2000 to 0.2444 parts by weight triethanolamine; and from 0.2000 to 0.2444 parts by weight gingko.

5. A lotion comprising: from 22.5000 to 27.5000 parts by weight hamamelis water; from 0.2250 to 0.2750 parts by weight ephedrine sulphate; from 0.0900 to 0.1100 parts by weight menthol crystals; from 4.0653 to 4.9687 parts by weight aloe powder; from 50.5701 to 61.8079 parts by weight purified water; from 0.3499 to 0.4277 parts by weight carbomer; from 4.0000 to 4.8888 parts by weight propylene glycol; from 0.1000 to 0.1222 parts by weight methylparaben; from 0.1000 to 0.1222 parts by weight propylparaben; from 0.1000 to 0.1222 parts by weight tetrasodium EDTA; from 0.7000 to 0.8555 parts by weight DEA cetyl phosphate; from 1.0000 to 1.2222 parts by weight stearic acid; from 0.2500 to 0.3055 parts by weight glyceryl stearate; from 0.2500 to 0.3055 parts by weight PEG 100 stearate; from 5.0000 to 6.1111 parts by weight C 12–15 alkyl benzoate; from 0.1000 to 0.1222 parts by weight jojoba oil; from 0.2000 to 0.2444 parts by weight ginseng; from 0.2000 to 0.2444 parts by weight imidazolidinyl urea; and from 0.2000 to 0.2444 parts by weight triethanolamine.

6. A lotion comprising: from 22.5000 to 27.5000 parts by weight hamamelis water; from 0.2250 to 0.2750 parts by weight ephedrine sulphate; from 0.0900 to 0.1100 parts by weight menthol crystals; from 4.0653 to 4.9687 parts by weight aloe powder; from 50.3702 to 61.5634 parts by weight purified water; from 0.3499 to 0.4277 parts by weight carbomer; from 4.0000 to 4.8888 parts by weight propylene glycol; from 0.1000 to 0.1222 parts by weight methylparaben; from 0.1000 to 0.1222 parts by weight propylparaben; from 0.1000 to 0.1222 parts by weight tetrasodium EDTA; from 0.7000 to 0.8555 parts by weight DEA cetyl phosphate; from 1.0000 to 1.2222 parts by weight stearic acid; from 0.2500 to 0.3055 parts by weight glyceryl stearate; from 0.2500 to 0.3055 parts by weight PEG 100 stearate; from 5.0000 to 6.1111 parts by weight C 12–15 alkyl benzoate; from 0.1000 to 0.1222 parts by weight jojoba oil; from 0.2000 to 0.2444 parts by weight ginseng; from 0.2000 to 0.2444 parts by weight imidazolidinyl urea; from 0.2000 to 0.2444 parts by weight triethanolamine; and from 0.2000 to 0.2444 parts by weight gingko.

7. A lotion comprising: about 10.0000 parts by weight hamamelis water; about 0.0050 parts by weight epinephrine hydrochloride; about 0.1000 parts by weight menthol crystals; about 4.5170 parts by weight aloe powder; about 71.4341 parts by weight purified water; about 0.3888 parts by weight carbomer; about 4.4444 parts by weight propylene glycol; about 0.1111 parts by weight methylparaben; about 0.1111 parts by weight propylparaben; about 0.1111 parts by weight tetrasodium EDTA; about 0.7777 parts by weight DEA cetyl phosphate; about 1.1111 parts by weight stearic acid; about 0.2777 parts by weight glyceryl stearate; about 0.2777 parts by weight PEG 100 stearate; about 5.5555 parts by weight C 12–15 alkyl benzoate; about 0.1111 parts by weight jojoba oil; about 0.2222 parts by weight ginseng; about 0.2222 parts by weight imidazolidinyl urea; and about 0.2222 parts by weight triethanolamine.

8. A lotion comprising: about 10.0000 parts by weight hamamelis water; about 0.0050 parts by weight epinephrine hydrochloride; about 0.1000 parts by weight menthol crystals; about 4.5170 parts by weight aloe powder; about 70.4341 parts by weight purified water; about 0.3888 parts by weight carbomer; about 4.4444 parts by weight propylene glycol; about 0.1111 parts by weight methylparaben; about 0.1111 parts by weight propylparaben; about 0.1111 parts by weight tetrasodium EDTA; about 0.7777 parts by weight DEA cetyl phosphate; about 1.1111 parts by weight stearic acid; about 0.2777 parts by weight glyceryl stearate; about 0.2777 parts by weight PEG 100 stearate; about 5.5555 parts by weight C 12–15 alkyl benzoate; about 0.1111 parts by weight jojoba oil; about 0.2222 parts by weight ginseng; about 0.2222 parts by weight imidazolidinyl urea; and about 0.2222 parts by weight triethanolamine; about 0.6000 parts by weight vanilla; and about 0.1000 parts by weight hyssop; and about 0.1000 parts by weight melissa; and about 0.1000 parts by weight angelica; and about 0.1000 parts by weight lavender.

9. A lotion comprising: about 10.0000 parts by weight hamamelis water; about 0.0050 parts by weight epinephrine hydrochloride; about 0.1000 parts by weight menthol crystals; about 4.5170 parts by weight aloe powder; about 70.2119 parts by weight purified water; about 0.3888 parts by weight carbomer; about 4.4444 parts by weight propylene glycol; about 0.1111 parts by weight methylparaben; about 0.1111 parts by weight propylparaben; about 0.1111 parts by weight tetrasodium EDTA; about 0.7777 parts by weight DEA cetyl phosphate; about 1.1111 parts by weight stearic acid; about 0.2777 parts by weight glyceryl stearate; about 0.2777 parts by weight PEG 100 stearate; about 5.5555 parts by weight C 12–15 alkyl benzoate; about 0.1111 parts by weight jojoba oil; about 0.2222 parts by weight ginseng; about 0.2222 parts by weight imidazolidinyl urea; and about 0.2222 parts by weight triethanolamine; about 0.6000 parts by weight vanilla; and about 0.1000 parts by weight hyssop; and about 0.1000 parts by weight melissa; and about 0.1000 parts by weight angelica; and about 0.1000 parts by weight lavender; and about 0.2222 parts by weight gingko.

10. A lotion comprising: about 10.0000 parts by weight hamamelis water; about 0.0050 parts by weight epinephrine hydrochloride; about 0.1000 parts by weight menthol crystals; about 4.5170 parts by weight aloe powder; about 71.2119 parts by weight purified water; about 0.3888 parts by weight carbomer; about 4.4444 parts by weight propylene glycol; about 0.1111 parts by weight methylparaben; about 0.1111 parts by weight propylparaben; about 0.1111 parts by weight tetrasodium EDTA; about 0.7777 parts by weight DEA cetyl phosphate; about 1.1111 parts by weight stearic acid; about 0.2777 parts by weight glyceryl stearate; about 0.2777 parts by weight PEG 100 stearate; about 5.5555 parts by weight C 12–15 alkyl benzoate; about 0.1111 parts by weight jojoba oil; about 0.2222 parts by weight ginseng; about 0.2222 parts by weight imidazolidinyl urea; and about 0.2222 parts by weight triethanolamine; and about 0.2222 parts by weight gingko.

11. A lotion comprising: about 25.0000 parts by weight hamamelis water; about 0.2500 parts by weight ephedrine sulphate; about 0.1000 parts by weight menthol crystals; about 4.5170 parts by weight aloe powder; about 56.1891 parts by weight purified water; about 0.3888 parts by weight carbomer; about 4.4444 parts by weight propylene glycol; about 0.1111 parts by weight methylparaben; about 0.1111 parts by weight propylparaben; about 0.1111 parts by weight tetrasodium EDTA; about 0.7777 parts by weight DEA cetyl phosphate; about 1.1111 parts by weight stearic acid; about 0.2777 parts by weight glyceryl stearate; about 0.2777 parts by weight PEG 100 stearate; about 5.5555 parts by weight C 12–15 alkyl benzoate; about 0.1111 parts by weight jojoba oil; about 0.2222 parts by weight ginseng; about 0.2222 parts by weight imidazolidinyl urea; and about 0.2222 parts by weight triethanolamine.

12. A lotion comprising: about 25.0000 parts by weight hamamelis water; about 0.2500 parts by weight ephedrine sulphate; about 0.1000 parts by weight menthol crystals; about 4.5170 parts by weight aloe powder; about 55.9669 parts by weight purified water; about 0.3888 parts by weight carbomer; about 4.4444 parts by weight propylene glycol; about 0.1111 parts by weight methylparaben; about 0.1111 parts by weight propylparaben; about 0.1111 parts by weight tetrasodium EDTA; about 0.7777 parts by weight DEA cetyl phosphate; about 1.1111 parts by weight stearic acid; about 0.2777 parts by weight glyceryl stearate; about 0.2777 parts by weight PEG 100 stearate; about 5.5555 parts by weight C 12–15 alkyl benzoate; about 0.1111 parts by weight jojoba oil; about 0.2222 parts by weight ginseng; about 0.2222 parts by weight imidazolidinyl urea; and about 0.2222 parts by weight triethanolamine; and about 0.2222 parts by weight gingko.

13. A method of making a lotion, comprising the steps of: heating from 64.2907 to 78.5775 parts by weight purified water; continuously mixing from 0.3499 to 0.4277 parts by weight carbomer into the water being heated until smooth and uniform; and then adding from 4.0653 to 4.9687 parts by weight aloe powder, from 4.0000 to 4.8888 parts by weight propylene glycol, from 0.1000 to 0.1222 parts by weight methylparaben, from 0.1000 to 0.1222 parts by weight propylparaben, from 0.1000 to 0.1222 parts by weight tetrasodium EDTA, into the smooth and uniform mixture while heating to a temperature of 75° C.; mixing into the 75° C. mixture from 0.7000 to 0.8555 parts by weight DEA cetyl phosphate, from 1.0000 to 1.2222 parts by weight stearic acid, from 0.2500 to 0.3055 parts by weight glyceryl stearate, from 0.2500 to 0.3055 parts by weight PEG 100 stearate, from 3.0000 to 3.6666 parts by weight C 12–15 alkyl benzoate; cooling the 75° C. mixture to 55° C.; mixing into the 55° C. mixture a solution having a temperature of 55° C. obtained from 2.0000 to 2.4444 parts by weight C 12–15 alkyl benzoate, from 0.0900 to 0.1100 parts per weight menthol crystals until smooth and uniform; cooling the 55° C. mixture to no more than 45° C.; mixing into the 45° C. mixture from 0.1000 to 0.1222 parts by weight jojoba oil; from 0.2000 to 0.2444 parts by weight ginseng; from 0.2000 to 0.2444 parts by weight imidazolidinyl urea; from 0.2000 to 0.2444 parts by weight triethanolamine and mixing into the 45° C. mixture from 9.0000 to 11.0000 parts by weight hamamelis water and from 0.0045 to 0.0055 parts by weight epinephrine hydrochloride.

14. A method of making a lotion comprising the steps of: heating from 63.3906 to 77.4774 parts by weight purified water; continuously mixing from 0.3499 to 0.4277 parts by weight carbomer into the water being heated until smooth and uniform; and then adding from 4.0653 to 4.9687 parts by weight aloe powder, from 4.0000 to 4.8888 parts by weight propylene glycol, from 0.1000 to 0.1222 parts by weight methylparaben, from 0.1000 to 0.1222 parts by weight propylparaben, from 0.1000 to 0.1222 parts by weight tetrasodium EDTA, into the smooth and uniform mixture while heating to a temperature of 75° C.; mixing into the 75° C. mixture from 0.7000 to 0.8555 parts by weight DEA cetyl phosphate, from 1.0000 to 1.2222 parts by weight stearic acid, from 0.2500 to 0.3055 parts by weight glyceryl stearate, from 0.2500 to 0.3055 parts by weight PEG 100 stearate, from 3.0000 to 3.6666 parts by weight C 12–15 alkyl benzoate; cooling the 75° C. mixture to 55° C.; mixing into the 55° C. mixture a solution having a temperature of 55° C. obtained from 2.0000 to 2.4444 parts by weight C 12–15 alkyl benzoate, from 0.0900 to 0.1100 parts per weight menthol crystals until smooth and uniform; cooling the 55° C. mixture to no more than 45° C.; mixing into the 45° C. mixture from 0.1000 to 0.1222 parts by weight jojoba oil; from 0.2000 to 0.2444 parts by weight ginseng; from 0.2000 to 0.2444 parts by weight imidazolidinyl urea; from 0.2000 to 0.2444 parts by weight triethanolamine and mixing into the 45° C. mixture from 9.0000 to 11.0000 parts by weight hamamelis water and from 0.0045 to 0.0055 parts by weight epinephrine hydrochloride; and adding and mixing into the 45° C. mixture from 0.5400 to 0.6600 parts by weight vanilla, and from 0.0900 to 0.1100 parts by weight hyssop, and from 0.0900 to 0.1100 parts by weight melissa, and from 0.0900 to 0.1100 parts by weight angelica, and from 0.0900 to 0.1100 parts by weight lavender.

15. A method of making a lotion comprising the steps of: heating from 63.1908 to 77.2330 parts by weight of purified water; continuously mixing from 0.3499 to 0.4277 parts by weight carbomer into the water being heated until smooth and uniform; and then adding from 4.0653 to 4.9687 parts by weight aloe powder, from 4.0000 to 4.8888 parts by weight propylene glycol, from 0.1000 to 0.1222 parts by weight methylparaben, from 0.1000 to 0.1222 parts by weight propylparaben, from 0.1000 to 0.1222 parts by weight tetrasodium EDTA, into the smooth and uniform mixture while heating to a temperature of 75° C.; mixing into the 75° C. mixture from 0.7000 to 0.8555 parts by weight DEA cetyl phosphate, from 1.0000 to 1.2222 parts by weight stearic acid, from 0.2500 to 0.3055 parts by weight glyceryl stearate, from 0.2500 to 0.3055 parts by weight PEG 100 stearate, from 3.0000 to 3.6666 parts by weight C 12–15 alkyl benzoate; cooling the 75° C. mixture to 55° C.; mixing into the 55° C. mixture a solution having a temperature of 55° C. obtained from 2.0000 to 2.4444 parts by weight C 12–15 alkyl benzoate, from 0.0900 to 0.1100 parts per weight menthol crystals until smooth and uniform; cooling the 55° C. mixture to no more than 45° C.; mixing into the 45° C. mixture from 0.1000 to 0.1222 parts by weight jojoba oil; from 0.2000 to 0.2444 parts by weight ginseng; from 0.2000 to 0.2444 parts by weight gingko; from 0.2000 to 0.2444 parts by weight imidazolidinyl urea; from 0.2000 to 0.2444 parts by weight triethanolamine and mixing into the 45° C. mixture from 9.0000 to 11.0000 parts by weight hamamelis water and from 0.0045 to 0.0055 parts by weight epinephrine hydrochloride; and adding and mixing into the 45° C. mixture from 0.5400 to 0.6600 parts by weight vanilla, and from 0.0900 to 0.1100 parts by weight hyssop, and from 0.0900 to 0.1100 parts by weight melissa, and from 0.0900 to 0.1100 parts by weight angelica, and from 0.0900 to 0.1100 parts by weight lavender.

16. A method of making a lotion comprising the steps of: heating from 64.0908 to 78.33330 parts by weight of purified water; continuously mixing from 0.3499 to 0.4277 parts by weight carbomer into the water being heated until smooth and uniform; and then adding from 4.0653 to 4.9687 parts by weight aloe powder, from 4.0000 to 4.8888 parts by weight propylene glycol, from 0.1000 to 0.1222 parts by weight methylparaben, from 0.1000 to 0.1222 parts by weight propylparaben, from 0.1000 to 0.1222 parts by weight tetrasodium EDTA, into the smooth and uniform mixture while heating to a temperature of 75° C.; mixing into the 75° C. mixture from 0.7000 to 0.8555 parts by weight DEA cetyl phosphate, from 1.0000 to 1.2222 parts by weight stearic acid, from 0.2500 to 0.3055 parts by weight glyceryl stearate, from 0.2500 to 0.3055 parts by weight PEG 100 stearate, from 3.0000 to 3.6666 parts by weight C 12–15 alkyl benzoate; cooling the 75° C. mixture to 55° C.; mixing into the 55° C. mixture a solution having a temperature of 55° C. obtained from 2.0000 to 2.4444 parts by weight C 12–15 alkyl benzoate, from 0.0900 to 0.1100 parts per weight menthol crystals until smooth and uniform; cooling the 55° C. mixture to no more than 45° C.; mixing into the 45° C. mixture from 0.1000 to 0.1222 parts by weight jojoba oil; from 0.2000 to 0.2444 parts by weight ginseng; from 0.2000 to 0.2444 parts by weight gingko; from 0.2000 to 0.2444 parts by weight imidazolidinyl urea; from 0.2000 to 0.2444 parts by weight triethanolamine and mixing into the 45° C. mixture from 9.0000 to 11.0000 parts by weight hamamelis water and from 0.0045 to 0.0055 parts by weight epinephrine hydrochloride.

17. A method of making a lotion, comprising the steps of: heating from 50.5701 to 61.8079 parts by weight purified water; continuously mixing from 0.3499 to 0.4277 parts by weight carbomer into the water being heated until smooth and uniform; and then adding from 4.0653 to 4.9687 parts by weight aloe powder, from 4.0000 to 4.8888 parts by weight propylene glycol, from 0.1000 to 0.1222 parts by weight methylparaben, from 0.1000 to 0.1222 parts by weight propylparaben, from 0.1000 to 0.1222 parts by weight tetrasodium EDTA, into the smooth and uniform mixture while heating to a temperature of 75° C.; mixing into the 75° C. mixture from 0.7000 to 0.8555 parts by weight DEA cetyl phosphate, from 1.0000 to 1.2222 parts by weight stearic acid, from 0.2500 to 0.3055 parts by weight glyceryl stearate, from 0.2500 to 0.3055 parts by weight PEG 100 stearate, from 3.0000 to 3.6666 parts by weight C 12–15 alkyl benzoate; cooling the 75° C. mixture to 55° C.; mixing into the 55° C. mixture a solution having a temperature of 55° C. obtained from 2.0000 to 2.4444 parts by weight C 12–15 alkyl benzoate, from 0.0900 to 0.1100 parts per weight menthol crystals until smooth and uniform; cooling the 55° C. mixture to no more than 45° C.; mixing into the 45° C. mixture from 0.1000 to 0.1222 parts by weight jojoba oil; from 0.2000 to 0.2444 parts by weight ginseng; from 0.2000 to 0.2444 parts by weight imidazolidinyl urea; from 0.2000 to 0.2444 parts by weight triethanolamine and mixing into the 45° C. mixture from 22.5000 to 27.5000 parts by weight hamamelis water and from 0.2250 to 0.2750 parts by weight ephedrine sulphate.

18. A method of making a lotion comprising the steps of: heating from 50.3702 to 61.5634 parts by weight of purified water; continuously mixing from 0.3499 to 0.4277 parts by weight carbomer into the water being heated until smooth and uniform; and then adding from 4.0653 to 4.9687 parts by weight aloe powder, from 4.0000 to 4.8888 parts by weight propylene glycol, from 0.1000 to 0.1222 parts by weight methylparaben, from 0.1000 to 0.1222 parts by weight propylparaben, from 0.1000 to 0.1222 parts by weight tetrasodium EDTA, into the smooth and uniform mixture while heating to a temperature of 75° C.; mixing into the 75° C. mixture from 0.7000 to 0.8555 parts by weight DEA cetyl phosphate, from 1.0000 to 1.2222 parts by weight stearic acid, from 0.2500 to 0.3055 parts by weight glyceryl stearate, from 0.2500 to 0.3055 parts by weight PEG 100 stearate, from 3.0000 to 3.6666 parts by weight C 12–15 alkyl benzoate; cooling the 75° C. mixture to 55° C.; mixing into the 55° C. mixture a solution having a temperature of 55° C. obtained from 2.0000 to 2.4444 parts by weight C 12–15 alkyl benzoate, from 0.0900 to 0.1100 parts per weight menthol crystals until smooth and uniform; cooling the 55° C. mixture to no more than 45° C.; mixing into the 45° C. mixture from 0.1000 to 0.1222 parts by weight jojoba oil; from 0.2000 to 0.2444 parts by weight ginseng; from 0.2000 to 0.2444 parts by weight gingko; from 0.2000 to 0.2444 parts by weight imidazolidinyl urea; from 0.2000 to 0.2444 parts by weight triethanolamine and mixing into the 45° C. mixture from 22.5000 to 27.5000 parts by weight hamamelis water and from 0.2250 to 0.2750 parts by weight ephedrine sulphate.

19. A lotion comprising: from 9.0000 to 11.0000 parts by weight hamamelis water; from 0.0045 to 0.0055 parts by weight epinephrine hydrochloride; from 0.0900 to 0.1100 parts by weight menthol crystals; from 4.0500 to 4.9500 parts by weight aloe powder; from 61.2405 to 74.8495 parts by weight purified water; from 4.5000 to 5.5000 parts by weight carbomer; from 3.6000 to 4.4000 parts by weight propylene glycol; from 0.1800 to 0.2200 parts by weight methylparaben; from 0.0900 to 0.1100 parts by weight propylparaben; from 0.9000 to 1.1000 parts by weight stearic acid; from 0.0900 to 0.1100 parts by weight tetrasodium EDTA; from 0.9000 to 1.1000 parts by weight DEA cetyl phosphate; from 4.5000 to 5.5000 parts by weight C 12–15 alkyl benzoate; from 0.0900 to 0.1100 parts by weight jojoba oil; from 0.1800 to 0.2200 parts by weight ginseng; from 0.1350 to 0.1650 parts by weight imidazolidinyl urea; and from 0.4500 to 0.5500 parts by weight triethanolamine.

20. A lotion comprising: from 9.0000 to 11.0000 parts by weight hamamelis water; from 0.0045 to 0.0055 parts by weight epinephrine hydrochloride; from 0.0900 to 0.1100 parts by weight menthol crystals; from 4.0500 to 4.9500 parts by weight aloe powder; from 60.9705 to 74.5195 parts by weight purified water; from 4.5000 to 5.5000 parts by weight carbomer; from 3.6000 to 4.4000 parts by weight propylene glycol; from 0.1800 to 0.2200 parts by weight methylparaben; from 0.0900 to 0.1100 parts by weight propylparaben; from 0.9000 to 1.1000 parts by weight stearic acid; from 0.0900 to 0.1100 parts by weight tetrasodium EDTA; from 0.9000 to 1.1000 parts by weight DEA cetyl phosphate; from 4.5000 to 5.5000 parts by weight C 12–15 alkyl benzoate; from 0.0900 to 0.1100 parts by weight jojoba oil; from 0.1800 to 0.2200 parts by weight ginseng; from 0.1350 to 0.1650 parts by weight imidazolidinyl urea; and from 0.4500 to 0.5500 parts by weight triethanolamine; and from 0.0900 to 0.1100 parts by weight vanilla; and from 0.0450 to 0.0550 parts by weight hyssop; from 0.0450 to 0.0550 parts by weight melissa; and from 0.0450 to 0.0550 parts by weight angelica; and from 0.0450 to 0.0550 parts by weight lavender.

21. A lotion comprising: about 10.0000 parts by weight hamamelis water; about 0.0050 parts by weight epinephrine hydrochloride; about 0.1000 parts by weight menthol crystals; about 4.5000 parts by weight aloe powder; about 68.0450 parts by weight purified water; about 5.0000 parts by weight carbomer; about 4.0000 parts by weight propylene glycol; about 0.2000 parts by weight methylparaben; about 0.1000 parts by weight propylparaben; about 1.0000 parts by weight stearic acid; about 0.1000 parts by weight tetrasodium EDTA; about 1.0000 parts by weight DEA cetyl phosphate; about 5.0000 parts by weight C 12–15 alkyl benzoate; about 0.1000 parts by weight jojoba oil; about 0.2000 parts by weight ginseng; about 0.1500 parts by weight imidazolidinyl urea; and about 0.5000 parts by weight triethanolamine.

22. A lotion comprising: about 10.0000 parts by weight hamamelis water; about 0.0050 parts by weight epinephrine hydrochloride; about 0.1000 parts by weight menthol crystals; about 4.5000 parts by weight aloe powder; about 67.7450 parts. by weight purified water; about 5.0000 parts by weight carbomer; about 4.0000 parts by weight propylene glycol; about 0.2000 parts by weight methylparaben; about 0.1000 parts by weight propylparaben; about 1.0000 parts by weight stearic acid; about 0.1000 parts by weight tetrasodium EDTA; about 1.0000 parts by weight DEA cetyl phosphate; about 5.0000 parts by weight C 12–15 alkyl benzoate; about 0.1000 parts by weight jojoba oil; about 0.2000 parts by weight ginseng; about 0.1500 parts by weight imidazolidinyl urea; and about 0.5000 parts by weight triethanolamine; and about 0.1000 parts by weight vanilla; and about 0.0500 parts by weight hyssop; and about 0.0500 parts by weight melissa; and about 0.0500 parts by weight angelica; and about 0.0500 parts by weight lavender.

23. A method of making a lotion, comprising the steps of: heating from 61.2405 to 74.8495 parts by weight purified water, continuously mixing from 4.5000 to 5.5000 parts by weight carbomer into the water being heated until smooth and uniform to make a first mixture; and then adding to said first mixture from 9.0000 to 11.0000 parts by weight hamamelis water, from 4.0500 to 4.9500 parts by weight aloe powder, from 3.6000 to 4.4000 parts by weight propylene glycol, from 0.1800 to 0.2200 parts by weight methylparaben, and from 0.0900 to 0.1100 parts by weight tetrasodium EDTA into the smooth and uniform mixture while heating to a temperature of 75° C.; mixing into the first mixture a second mixture at a temperature of 75° C. made from 0.9000 to 1.1000 parts by weight DEA cetyl phosphate, and from 0.9000 to 1.1000 parts by weight stearic acid, and from 4.5000 to 5.5000 parts by weight C 12–15 alkyl benzoate, and from 0.0900 to 0.1100 parts by weight jojoba oil, and from 0.1800 to 0.2200 parts by weight ginseng, and from 0.0900 to 0.1100 parts by weight propylparaben; mixing into the combined first and second mixtures from 0.4500 to 0.5500 parts by weight of triethanolamine; cooling the combined first and second mixtures with triethanolamine to 40° C.; mixing into the combined first and second mixtures with triethanolamine from 0.0900 to 0.1100 parts by weight of menthol crystals; mixing into the combined first and second mixtures with triethanolamine and menthol crystals a third mixture made from 0.0045 to 0.0055 parts by weight epinephrine hydrochloride and from 0.1350 to 0.1650 parts by weight imidazolidinyl urea at a temperature of about 40° C. to make a final mixture; and cooling the final mixture to a temperature of about 25° C.

24. A method of making a lotion, comprising the steps of: heating from 60.9705 to 74.5195 parts by weight purified water, continuously mixing from 4.5000 to 5.5000 parts by weight carbomer into the water being heated until smooth and uniform to make a first mixture; and then adding to said first mixture from 9.0000 to 11.0000 parts by weight hamamelis water, from 4.0500 to 4.9500 parts by weight aloe powder, from 3.6000 to 4.4000 parts by weight propylene glycol, from 0.1800 to 0.2200 parts by weight methylparaben, and from 0.0900 to 0.1100 parts by weight tetrasodium EDTA into the smooth and uniform mixture while heating to a temperature of 75° C.; mixing into the first mixture a second mixture at a temperature of 75° C. made from 0.9000 to 1.1000 parts by weight DEA cetyl phosphate, and from 0.9000 to 1.1000 parts by weight stearic acid, and from 4.5000 to 5.5000 parts by weight C 12–15 alkyl benzoate, and from 0.0900 to 0.1100 parts by weight jojoba oil, and from 0.1800 to 0.2200 parts by weight ginseng, and from 0.0450 to 0.0550 parts by weight hyssop, and from 0.0450 to 0.0550 parts by weight melissa, and from 0.0450 to 0.0550 parts by weight angelica, and from 0.0900 to 0.1100 parts by weight propylparaben; mixing into the combined first and second mixtures from 0.4500 to 0.5500 parts by weight of triethanolamine; cooling the combined first and second mixtures with triethanolamine to 40° C.; mixing into the combined first and second mixtures with triethanolamine a third mixture made from 0.0900 to 0.1100 parts by weight of menthol crystals and from 0.0900 to 0.1100 parts by weight vanilla and from 0.0450 to 0.0550 parts by weight lavender at a temperature of about 40° C.; mixing into the combined first and second and third mixtures with triethanolamine a fourth mixture made from 0.0045 to 0.0055 parts by weight epinephrine hydrochloride and from 0.1350 to 0.1650 parts by weight imidazolidinyl urea at a temperature of about 40° C. to make a final mixture; and cooling the final mixture to a temperature of about 25° C.

* * * * *